United States Patent
Fonte et al.

(10) Patent No.: US 10,524,837 B2
(45) Date of Patent: Jan. 7, 2020

(54) THREE DIMENSIONAL SPACER FABRIC TO INCREASE THE HOLDING POWER OF SCREWS

(71) Applicant: Arthrex, Inc., Naples, FL (US)

(72) Inventors: Matthew Fonte, Concord, MA (US); Matthew Palmer, Medford, MA (US); Robert Devaney, Auburndale, MA (US)

(73) Assignee: Arthrex, Inc., Naples, FL (US)

( * ) Notice: Subject to any disclaimer, the term of this patent is extended or adjusted under 35 U.S.C. 154(b) by 170 days.

(21) Appl. No.: 15/652,693

(22) Filed: Jul. 18, 2017

(65) Prior Publication Data

US 2018/0028232 A1    Feb. 1, 2018

Related U.S. Application Data

(60) Provisional application No. 62/366,814, filed on Jul. 26, 2016.

(51) Int. Cl.

| | | |
|---|---|---|
| *A61B 17/68* | (2006.01) | |
| *A61B 17/86* | (2006.01) | |
| *A61L 27/06* | (2006.01) | |
| *A61L 31/16* | (2006.01) | |
| *A61L 31/14* | (2006.01) | |
| *A61L 31/02* | (2006.01) | |
| *A61B 17/00* | (2006.01) | |

(52) U.S. Cl.
CPC ............ *A61B 17/68* (2013.01); *A61B 17/686* (2013.01); *A61B 17/8625* (2013.01); *A61L 27/06* (2013.01); *A61L 31/026* (2013.01); *A61L 31/146* (2013.01); *A61L 31/16* (2013.01); *A61B 2017/00867* (2013.01); *A61B 2017/8655* (2013.01); *A61L 2300/112* (2013.01); *A61L 2300/412* (2013.01)

(58) Field of Classification Search
CPC ..... A61B 17/68; A61B 17/86; A61B 17/8625; A61L 31/14; A61L 31/16; A61L 31/146
See application file for complete search history.

(56) References Cited

U.S. PATENT DOCUMENTS

| | | | | |
|---|---|---|---|---|
| 6,746,483 B1* | 6/2004 | Bojarski | ............ | A61B 17/0401 |
| | | | | 623/13.14 |
| 6,827,743 B2* | 12/2004 | Eisermann | ............. | A61B 17/68 |
| | | | | 623/23.54 |
| 8,956,394 B1* | 2/2015 | McDonnell | .......... | A61B 17/686 |
| | | | | 606/300 |

\* cited by examiner

*Primary Examiner* — Christopher J Beccia
(74) *Attorney, Agent, or Firm* — Carlson, Gaskey & Olds, P.C.

(57) ABSTRACT

A method of increasing a pullout force of a threaded fastener in osteoporotic bone includes drilling a hole in the bone. The spacer fabric is impregnated with a bone growth agent. A tube of the spacer fabric is sized to the hole in the bone. The tube of the spacer fabric is inserted in the hole of the bone. The spacer fabric is made from Nitinol wire. A threaded fastener is inserted into a central lumen of the tube of the spacer fabric to provide a rigid structure. The bone is grown into the spacer fabric.

7 Claims, 4 Drawing Sheets

THREE DIMENSIONAL SPACER FABRIC TO INCREASE THE HOLDING POWER OF SCREWS

CROSS REFERENCE TO RELATED APPLICATIONS

This patent application claims priority to and the benefit of prior U.S. Provisional Patent Application Ser. No. 62/366,814 filed on Jul. 26, 2016, the entire disclosure of which is hereby incorporated by reference.

BACKGROUND OF THE INVENTION

Bone fractures are traditionally treated with screws, staples, and/or plates to re-approximate the fractured surfaces and generate compression between bone fragments. The bone mineral density of osteoporotic and osteopenic bone is less than the bone mineral density of healthy bone, and therefore screws do not strongly grip into this soft bone. Clinically, to address this fixation problem, surgeons use multiple screws and/or larger diameter screws. Surgeons may switch from using a cortical bone screw to using a cancellous bone screw. Cancellous bone screws have a larger diameter and much deeper threads that can better grip the soft bone. However, larger screws weaken the overall anatomy and create regions of high stress.

Therefore, there is a need for other methods to increase the ability of screws to grip osteoporotic bone.

SUMMARY

In one example, a method of increasing a pullout force of a threaded fastener in osteoporotic bone includes drilling a hole in the bone. The spacer fabric is impregnated with a bone growth agent. A tube of the spacer fabric is sized to the hole in the bone. The tube of the spacer fabric is inserted in the hole of the bone. The spacer fabric is made from Nitinol wire. A threaded fastener is inserted into a central lumen of the tube of the spacer fabric to provide a rigid structure. The bone is grown into the spacer fabric.

In another example, a method of increasing a pullout force of a threaded fastener in osteoporotic bone includes drilling a hole in the bone. A tube of spacer fabric is inserted in the hole of the bone. A threaded fastener is inserted into a central lumen of the tube of the spacer fabric to provide a rigid structure.

In another embodiment according to any of the previous embodiments, the spacer fabric is made from a metallic wire.

In another embodiment according to any of the previous embodiments, the spacer fabric is made from Nitinol wire.

In another embodiment according to any of the previous embodiments, the method includes impregnating the spacer fabric with a bone growth agent.

In another embodiment according to any of the previous embodiments, the method includes sizing the tube of the spacer fabric to the hole in the bone.

In another embodiment according to any of the previous embodiments, the method includes growing the bone into the spacer fabric.

In another example, a porous structure includes a structure forming a tube having a central lumen. The tube is located in a hole in a bone. A threaded fastener is received in the central lumen of the tube. The threaded fastener expands the structure outwardly to apply pressure against the bone. The structure expands inwardly to apply pressure against the threaded fastener.

In another embodiment according to any of the previous embodiments, the structure is made from spacer fabric.

In another embodiment according to any of the previous embodiments, the spacer fabric is knitted metallic wire.

In another embodiment according to any of the previous embodiments, the spacer fabric is knitted Nitinol wire.

In another embodiment according to any of the previous embodiments, the spacer fabric includes a top fabric layer, a bottom fabric layer, and interconnecting filler fibers therebetween.

In another embodiment according to any of the previous embodiments, the spacer fabric is impregnated with a bone growth agent.

In another embodiment according to any of the previous embodiments, the bone growth agent is one of hydroxyapatite or calcium phosphate.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION

Figure 1A:
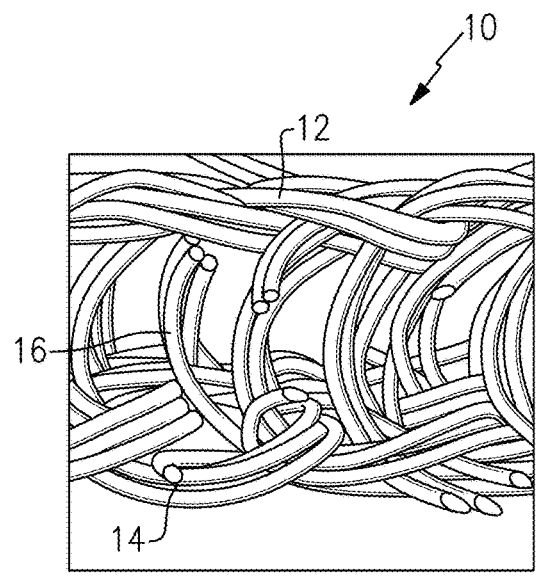
FIG. 1a illustrates a lateral face of a spacer fabric.
Figure 1B:
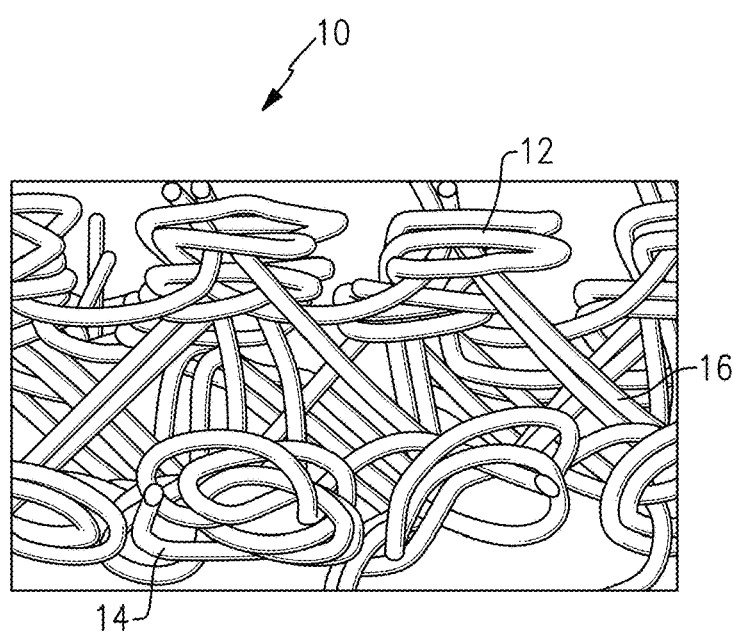
FIG. 1b illustrates a transverse face of the spacer fabric.
Figure 1C:
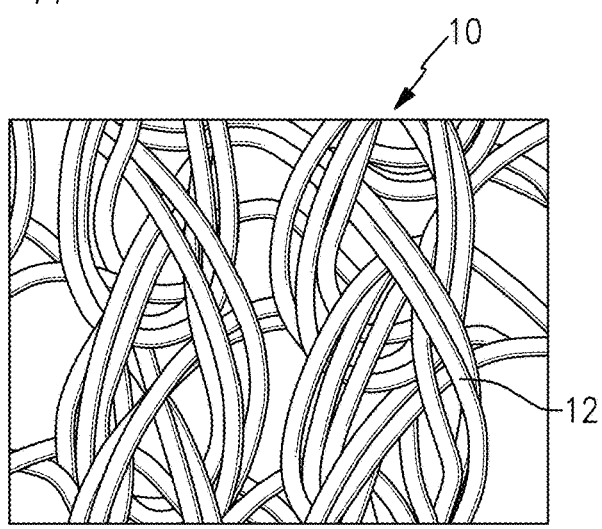
FIG. 1c illustrates a top face of the spacer fabric.

As shown in FIGS. 1a, 1b and 1c, a spacer fabric 10 is a three-dimensional knit structure that include a first fabric layer 12, a second fabric layer 14, and yarns 16 interconnecting the first fabric layer 12 and the second fabric layer 14. A portion of the yarns 16 interconnecting the first fabric layer 12 and the second fabric layer 14 are perpendicular to each of the first fabric layer 12 and the second fabric layer 14, while the remaining interconnecting yarns 16 are disposed at a non-perpendicular angle between the first fabric layer 12 and the second fabric layer 14. The spacer fabric 10 can be knit in flat sheets or in tubes. The structure is inherently compressible and elastic.

The spacer fabric 10 can be knit from metallic wire or non-metallic, polymeric fibers. It is possible to knit the spacer fabric 10 from Nitinol, a shape memory/superelastic Nickel-Titanium Alloy. A spacer fabric 10 of Nitinol can also be crush resistant.

Nitinol (Nickel alloy, Naval Ordnance Laboratory) exhibits two unique properties: shape memory and superelasticty (also called pseudoelasticy). Shape memory refers to the ability of Nitinol to undergo deformation at one temperature, then recover its original, un-deformed shape upon heating to a temperature above its "transformation temperature." Superelasticity occurs above its transformation temperature. In this case, no heating is necessary to recover the un-deformed shape. Nitinol exhibits enormous elasticity and is about 30 times more elastic than structural steel, stainless steel, and titanium.

Figure 2:
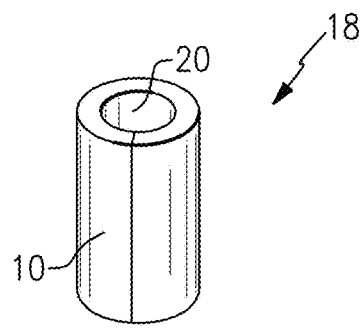
FIG. 2 illustrates the spacer fabric shaped as a tube.

As shown in FIG. 2, the spacer fabric 10 is manufactured as a tube or as a sheet that is rolled into a tube. The tube 18 can be used to increase the gripping ability of a threaded fastener 32 in osteopenic and/or osteoporotic bone. The tube 18 has a central lumen 20.

Figure 3:
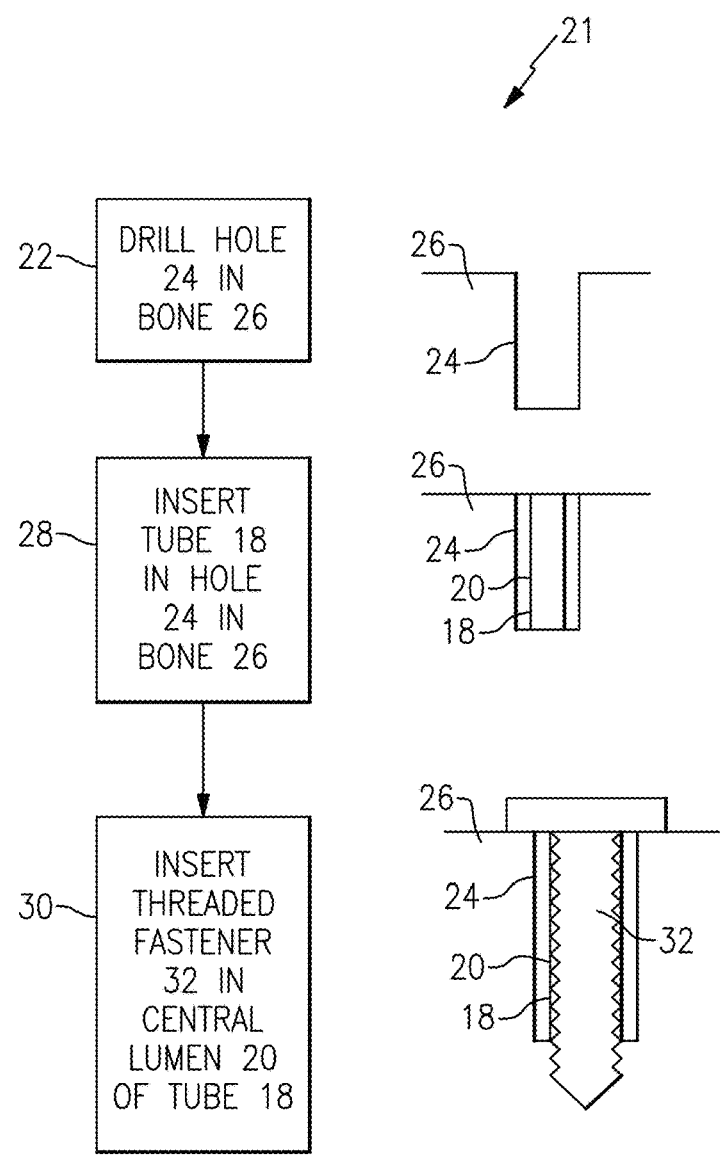
FIG. 3 illustrates a method of inserting a threaded fastener into bone.

FIG. 3 shows a method 21 of inserting a threaded fastener 32 into a bone 26. In a first step 22, a surgeon drills a hole 24 in a bone 26. In step 28, the surgeon then sizes the tube 18 of the spacer fabric 10 and presses the tube 18 into the hole 24 in the bone 26. The tube 18 of spacer fabric 10 is pressed into the drilled hole 24 to increase the holding power of the threaded fastener 32. Finally, in step 30, the surgeon can insert a threaded fastener 32, such as a screw, into the central lumen 20 of the tube 18 of the spacer fabric 10. Insertion of the threaded fastener 32 into the central lumen 20 of the tube 18 of the spacer fabric 10 presses the spacer fabric 10 into the bone 26 and provides a rigid structure for the threaded fastener 32 to grip onto, increasing the pullout force of the threaded fastener 32.

The spacer fabric 10 will conform to the threaded fastener 32, allowing the threaded fastener 32 to thread into the central lumen 20 and pushing the spacer fabric 10 into the soft bone stock. As the spacer fabric 10 is highly porous, the bone 26 can use the spacer fabric 10 as a scaffold and grow into the spacer fabric 10.

In one example, the spacer fabric 10 is made of Nitinol. Bone prefers to grow onto metallic surfaces rather than polymeric surfaces. As Nitinol is superelastic, a Nitinol spacer fabric 10 will attempt to expand in vivo when pressed into a hole. The expansion provides chronic pressure against a bone surface, stimulating osseointegration. The expansion also generates a compressive force on a threaded fastener 32, increasing the pull out force of the threaded fastener 32.

Figure 4:
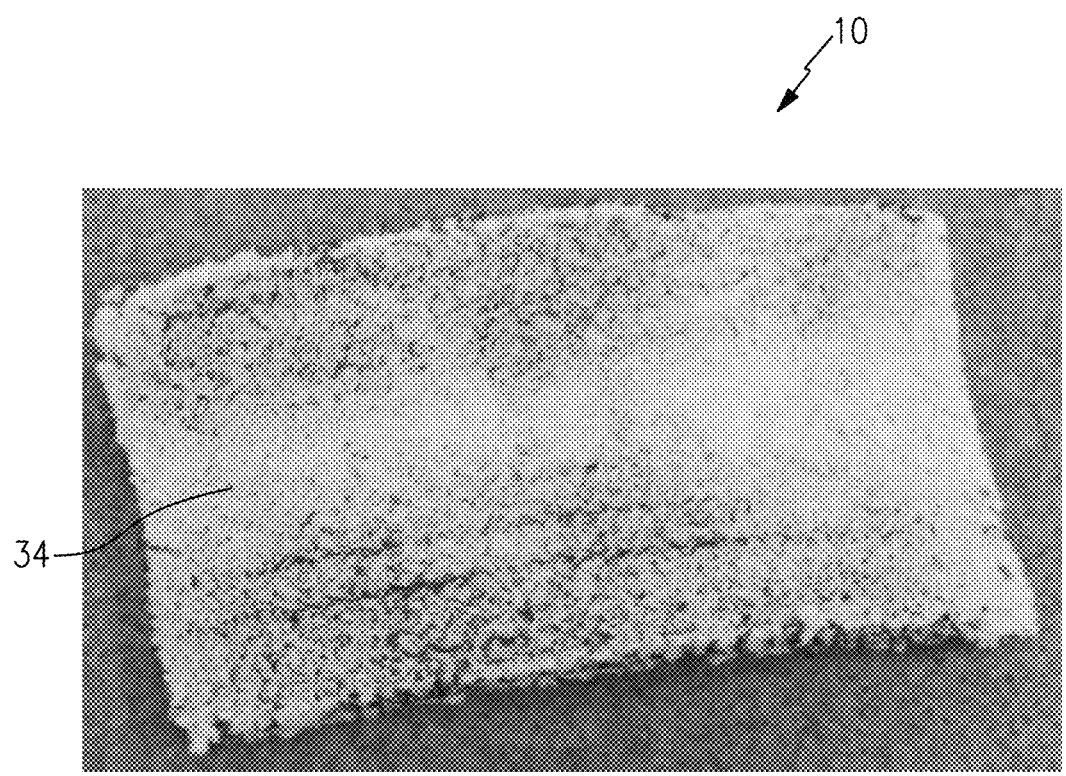
FIG. 4 illustrates the spacer fabric loaded with biologically active agents.

As shown in FIG. 4, the spacer fabric 10 can be loaded with biologically active agents 34 to enhance bone ingrowth and deliver bone growth agents locally to osteoporotic bone. The spacer fabric 10 makes an excellent delivery device because it is highly porous. In one example, the spacer fabric 10 is coated directly with hydroxyapatite. In another example, pores of the spacer fabric 10 are filled with a slurry of bone growth agent (calcium phosphate), methylcellulose, and glycerol. When this slurry is frozen and lyophilized, the resorbable pliable bone growth agents 34 remain within the pores of the spacer fabric 10.

Figure 5:
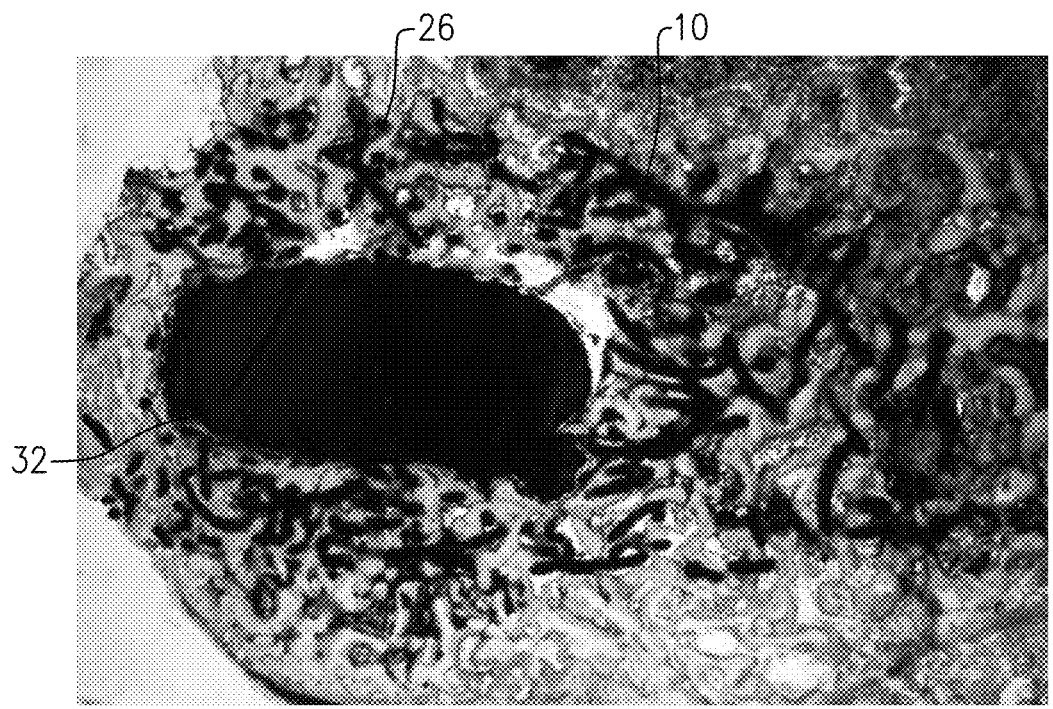
FIG. 5 illustrates a bone and the spacer fabric after 12 weeks of healing.

FIG. 5 shows the bone 26 and the spacer fabric 10 over time. Bone 26 rapidly integrates with the Nitinol spacer fabric 10. The Nitinol spacer fabric 10 is shown as a darkened area that is integrated with the bone 26. The threaded fastener 32 in the central lumen 20 is implanted into a lateral femoral condyle of a rabbit for 12 weeks.

In bench top testing, a sleeve of Nitinol spacer fabric 10 wrapped around a threaded fastener 32 increases the pullout force of the threaded fastener 32 compared to the same threaded fastener 32 in osteoporotic bone. Testing was conducted using a 10 lb/ft3 polyurethane bone substitute. A tight hole 24 was drilled into the bone 26, and the cancellous bone threaded fastener 32 was threaded into the bone 26. The threaded fastener 32 was pulled out of the bone 26 using a tensile testing machine. This was compared to a fragment of simulated bone 26 where a larger diameter hole 24 (to simulate poor bone quality) was drilled, a tube 18 of Nitinol spacer fabric 10 was inserted into the hole 24, and the same diameter threaded fastener 32 was threaded into the hole 24. The pullout force of the osteoporotic spacer fabric sample (297.3698 N with a 4.0 mm threaded fastener) had the same pullout force as the non-osteoporotic spacer fabric sample (303.4682 N with a 4.0 mm threaded fastener).

In one example, a method of increasing a pullout force of a threaded fastener in osteoporotic bone includes drilling a hole in the bone. The spacer fabric is impregnated with a bone growth agent. A tube of the spacer fabric is sized to the hole in the bone. The tube of the spacer fabric is inserted in the hole of the bone. The spacer fabric is made from Nitinol wire. A threaded fastener is inserted into a central lumen of the tube of the spacer fabric to provide a rigid structure. The bone is grown into the spacer fabric.

In another example, a method of increasing a pullout force of a threaded fastener in osteoporotic bone includes drilling a hole in the bone. A tube of spacer fabric is inserted in the hole of the bone. A threaded fastener is inserted into a central lumen of the tube of the spacer fabric to provide a rigid structure.

In another embodiment according to any of the previous embodiments, the spacer fabric is made from a metallic wire.

In another embodiment according to any of the previous embodiments, the spacer fabric is made from Nitinol wire.

In another embodiment according to any of the previous embodiments, the method includes impregnating the spacer fabric with a bone growth agent.

In another embodiment according to any of the previous embodiments, the method includes sizing the tube of the spacer fabric to the hole in the bone.

In another embodiment according to any of the previous embodiments, the method includes growing the bone into the spacer fabric.

In another example, a porous structure includes a structure forming a tube having a central lumen. The tube is located in a hole in a bone. A threaded fastener is received in the central lumen of the tube. The threaded fastener expands the structure outwardly to apply pressure against the bone. The structure expands inwardly to apply pressure against the threaded fastener.

In another embodiment according to any of the previous embodiments, the structure is made from spacer fabric.

In another embodiment according to any of the previous embodiments, the spacer fabric is knitted metallic wire.

In another embodiment according to any of the previous embodiments, the spacer fabric is knitted Nitinol wire.

In another embodiment according to any of the previous embodiments, the spacer fabric includes a top fabric layer, a bottom fabric layer, and interconnecting filler fibers therebetween.

In another embodiment according to any of the previous embodiments, the spacer fabric is impregnated with a bone growth agent.

In another embodiment according to any of the previous embodiments, the bone growth agent is one of hydroxyapatite or calcium phosphate.

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method of increasing a pullout force of a threaded fastener in osteoporotic bone, the method comprising:
  drilling a hole in osteoporotic bone;
  inserting a tube of spacer fabric in the hole of the bone, wherein the spacer fabric is made from knitted Nitinol wire and comprises a first fabric layer, a second fabric layer, and yarns interconnecting the first fabric layer and the second fabric layer, wherein a portion of the yarns are disposed at a perpendicular angle between interconnecting the first fabric layer and the second fabric layer, and the spacer fabric contacts the bone; and inserting a threaded fastener into a central lumen of the tube of the spacer fabric, wherein the threaded fastener grips onto the spacer fabric.

2. The method as recited in claim 1, wherein the spacer fabric is impregnated with a bone growth agent.

3. A porous structure comprising:

a knitted Nitinol wire structure forming a tube having a central lumen, wherein the structure comprises a top fabric layer, a bottom fabric layer, and yarns interconnecting the top fabric layer and the bottom fabric layer, wherein a portion of the yarns are disposed at a perpendicular angle between interconnecting the first fabric layer and the second fabric layer, wherein pores of the spacer fabric comprise a slurry of calcium phosphate, methylcellulose, and glycerol.

4. The method as recited in claim 2, wherein the bone growth agent is one of hydroxyapatite or calcium phosphate.

5. The method as recited in claim 1, wherein pores of the spacer fabric comprise a slurry of calcium phosphate, methylcellulose, and glycerol.

6. The method as recited in claim 5, wherein the slurry is frozen and lyophilized.

7. The porous structure as recited in claim 3, wherein the slurry is frozen and lyophilized.

\* \* \* \* \*